United States Patent [19]

Itzkan

[11] Patent Number: 4,733,660
[45] Date of Patent: Mar. 29, 1988

[54] LASER SYSTEM FOR PROVIDING TARGET SPECIFIC ENERGY DEPOSITION AND DAMAGE

[75] Inventor: Irving Itzkan, Boston, Mass.

[73] Assignee: Medical Laser Research and Development Corporation, Malden, Mass.

[21] Appl. No.: 940,195

[22] Filed: Dec. 10, 1986

Related U.S. Application Data

[63] Continuation of Ser. No. 638,419, Aug. 7, 1984, abandoned.

[51] Int. Cl.$^4$ .............................................. A61B 17/36
[52] U.S. Cl. ............................ 128/303.1; 219/121 LV
[58] Field of Search ......................................... 128/4–8, 128/303.1, 395–398; 219/121 LA, 121 LR, 121 LU, 121 LV

[56] References Cited

U.S. PATENT DOCUMENTS

| | | | |
|---|---|---|---|
| 3,434,476 | 3/1969 | Shaw et al. | 128/303.1 |
| 3,456,651 | 7/1969 | Snert | 128/303.1 |
| 3,642,007 | 2/1972 | Roberts et al. | 128/395 |
| 3,653,384 | 4/1972 | Swope | 128/303.1 |
| 3,664,730 | 5/1972 | Cardna | 128/395 |
| 3,710,798 | 1/1973 | Bredemeier | 128/303.1 |
| 3,769,963 | 11/1973 | Goldman et al. | 128/303.1 |
| 3,799,657 | 3/1974 | Dager et al. | 219/121 LU |
| 3,821,510 | 6/1974 | Munchergan | 128/303.1 |
| 3,906,953 | 9/1975 | Wallace et al. | 128/303.1 |
| 3,910,276 | 10/1975 | Polanyi et al. | 128/303.1 |
| 3,986,767 | 10/1976 | Rexer et al. | 219/121 LV |
| 4,069,823 | 1/1978 | Isakov et al. | 128/303.1 |
| 4,079,230 | 3/1978 | Miyauchi et al. | 219/121 LR |
| 4,240,431 | 12/1980 | Komiya | 128/303.1 |
| 4,316,467 | 2/1982 | Muckerheide | 128/303.1 |
| 4,367,017 | 1/1983 | Jimbou et al. | 219/121 LV |
| 4,408,602 | 10/1983 | Nakajima | 128/303.1 |
| 4,461,947 | 7/1984 | Ward | 219/121 LU |
| 4,517,963 | 5/1985 | Michel | 128/6 |

FOREIGN PATENT DOCUMENTS

| | | | |
|---|---|---|---|
| 0075912 | 6/1983 | European Pat. Off. | 128/303.1 |
| 0130950 | 9/1985 | European Pat. Off. | |
| 2062951 | 9/1971 | Fed. Rep. of Germany | 128/6 |

OTHER PUBLICATIONS

"Histology of Port Wine Stains Following Argon Laser Treatment", Apfelberg et al.
"Port Wine Stains and the Response to Argon Laser Therapy: Successful ..., and Biopsy", Noe et al, Plastic & Recon. Surg. Eab 1980.
"Healing of Port Wine Stains After Argon Laser Therapy" Arch Sernitol, Aug. 1981, Finey et al.
"Histology of Port–Wine Stains Treated with $CO_2$ Laser", Bueckes et al.
"Laser Balloon Argloplisty ... " Serur et al., Abstracts of the 58th Session 1985.
"In VNO ... " Sanborn et al., Abstracts of the 58th Session 1985.
"Multispot Laser Photocoagulation System Using a Fiber Bundle Scanner" Applied Optics, Oct. 1982, Fujii et al.
"$CO_2$ Laser Treatment of Port–Wine Stains: A Preliminary Report", Ratz et al., J. Dem, Dec. 1982.
"Microvasculture Can Be Selectively Damaged Using Dye Lasers: A Basic ... Human Skin", Lasers in Serg. & Med. 1981.

Primary Examiner—Max Hindenburg
Attorney, Agent, or Firm—Weingarten, Schurgin, Gagnebin & Hayes

[57] ABSTRACT

A hand piece for use with a laser includes a scanning mechanism which controls dosimetry of radiation applied to a target area which is adjustable to limit thermal diffusion from the light absorbing portion of the irradiated target site for selective target specific energy deposition. When used for dermatologic purposes, the adjustable scanning mechanism permits radiation to impinge on tissue for a predetermined period of time for the selective necrosis of highly-filled blood vessels, while leaving adjacent tissue and empty blood vessels undamaged. The dwell time of the laser beam is designed to match the diffusion time for thermal destruction of the wall of the abnormal vessel, with the dwell time adjusted by the scanning rate.

12 Claims, 8 Drawing Figures

LASER SYSTEM FOR PROVIDING TARGET SPECIFIC ENERGY DEPOSITION AND DAMAGE

This application is a continuation of application Ser. No. 638,419, filed Aug. 7, 1984, abandoned 12/10/86.

FIELD OF INVENTION

This invention relates to medical treatment and, more particularly, to the control of a laser output in such a way as to limit the dwell time on any particular portion of the tissue, thus permitting target specific energy deposition and damage which is selective and controllable.

BACKGROUND OF THE INVENTION

There are many medical conditions, the treatment of which is substantially improved by being able to control the deposition of laser energy in a specific target tissue in order to damage that target tissue while sparing the adjacent tissue. While those in the past have utilized lasers, particularly in the port wine stain (PWS) syndrome, to destroy blood vessels, the problem associated with such systems is that the dwell time of the laser over the target produces significant thermal diffusion which damages not only the abnormal PWS vessels which are ectatic, i.e., dilated and filled, and strongly absorb the radiation, the ones producing the wine stain, but also damages a significant depth of the dermis such that scabbing and sloughing occurs as a consequence of treatment. Additionally, the use of an anesthetic is prescribed because of the amount of energy imparted to the target area which is painful to the patient. It will be appreciated that the desired treatment for port wine stains is to necrose only those vessels producing the stain while leaving most of the surrounding collagen and the normal vessels undamaged. This translates into control of thermal diffusion, which up until the present time has been difficult either because of the relatively long pulse lengths of the shuttered CW lasers utilized or because of the relatively short pulse lengths of the dye lasers which do not completely destroy the abnormal vessels. Consequently, no successful control has heretofore been exercised to limit the volume affected by thermal diffusion. The result of the lack of control is that lasers which dwell on a given target area for 20 milliseconds or more produce so much thermal diffusion that scabbing and sloughing of the epidermis and portions of dermis are produced regardless of wavelength, assuming any kind of therapeutic levels are introduced to the target area.

By way of further background, if it is desirable to destroy abnormal tissue contained within the volume of normal tissue and spare the overlying normal layer, differential absorption of the light is required. This can be obtained by either intrinsic optical qualities of the target or tagging with some exogenous chromophore. In the latter case, the wavelength or color of the laser must be selected on the basis of the absorption spectra of both the target and the surrounding tissue. In other words, it should be a wavelength where the target tissue is a good absorber and the surrounding tissue is a poor absorber. Moreover, the irradiation time must be selected on the basis of the thermal properties of the target and surrounding tissue and the geometric shape and dimensions of the tissue structure.

Thus, in some cases the target tissue is distinguished from surrounding tissue by a difference in absorption spectra either due to a naturally-occurring chromophore (absorbing molecule) or due to the selective deposition of some dye used in the treatment regimen. One important example of such a target tissue present throughout the body is the vasculature which contains erythrocytes. The erythrocytes contain hemoglobin, a naturally-occurring chromophore with a broad usable absorption band in the visible. The entire range of visible wavelengths shorter than approximately 600 nm (nanometers) and extending into the ultraviolet is available to purposely inflict damage to target tissues containing this chromophore. The specific wavelength selected depends on the relative effects of scattering, which varies with wavelength; the presence of other chromophores, such as melanin, in the adjacent or overlying tissues; and the availability of light sources.

In selecting the exposure time, one is limited by the time which will confine thermal damage due to heat transport to an acceptable distance from the target. For the treatment of port wine stains, it is desirable to be in the regime where the dominant mechanism for heat transport is conduction. A characteristic thermal diffusion length for heat conduction is given by $$L^2 = 4Kt$$

where L = distance that heat diffuses; K = thermal diffusivity coefficient; and t = time allowed for diffusion.

This formula varies slightly with the geometry of the irradiated target in surrounding media, but the variations are not significant. A typical thermal diffusivity coefficient for biological tissues is 0.0015 cm$^2$/second.

Considering, for example, the treatment of port wine stains, a type of hemangioma that consists of hypertrophic capillaries in the dermis causing a pink, red or purple coloring of the skin, the pink and red lesions are high in erythrocytes carrying oxygenated hemoglobin (HbO$_2$), while the purple lesions contain large quantities of deoxygenated hemoglobin (Hb). The lesions are characterized as consisting of abnormal capillary structure with the capillaries varing in diameter, the mean diameter being about 50 micrometers. The wall of the vessel, however, is only a few micrometers thick. The average vessel spacing is 100 micrometers. In order to damage the vessel containing the target hemoglobin, its wall, and a small portion of collagen surrounding the wall, the latter two being relatively free of chromophore, it is important to select an exposure time corresponding to thermal diffusion over a characteristic length slightly greater than the wall thickness. This, in general, refers to the delivery of radiation to a given target area of less than one millisecond. Those prior art devices which deliver 20 milliseconds or more cause damage due to thermal diffusion of heat to a distance even greater than the vessel spacing. Thus the entire tissue bulk is heated by the vessel network embedded within it and the damage is not at all selective.

J. L. Finley, S. H. Barsky and D. E. Geer in an article entitled "Healing of Port Wine Stains After Argon Laser Therapy," *Archives of Dermatology*, 1981, Volume 117, pps. 486–489, and J. L. Ratz, P. L. Bailin, and H. L. Levine in an article entitled "CO$_2$ Laser Treatment of Port-Wine Stains: A Preliminary Report," *J. Dermatol. Surg. Oncol.* 1982, Vol. 8, No. 12, pps 1039–1044, describe both argon lasers and carbon dioxide lasers used in the clinical treatment of port wine stains. Neither of these provide an optimal treatment modality as the dwell time is not limited to prevent thermal diffusion.

It will be appreciated that the CO₂ laser radiation whose wavelength is approximately 10 micrometers is very strongly absorbed in water and most proteins. In port wine stains, both the abnormal vasculature and the surrounding dermal tissues are approximately 90% water and consequently absorb the incident laser radiation and are heated to the point of thermal necrosis. Thus this treatment does not involve any specificity of damage. The necrotic tissue eventually sloughs off and is replaced via the normal healing process by scar tissue formation. Since the scar tissue formed is usually flat and white, it is often more acceptable to the patient that the original dark and, sometimes, hypertrophic lesion.

Present treatment of port wine stains with the argon laser is performed using comparatively long pulse times. Because of this, heat has time to diffuse to the surrounding tissue, and the effect observed is the same as for the CO₂ laser in which radiation is uniformly absorbed in both vascular and surrounding tissue. The similarity of clinical results with the CO₂ and the long pulse argon lasers has been noticed and documented in an article by J. W. Buecker, J. L. Ratz and D. F. Richfield entitled "Histology of Port Wine Stains Treated with CO₂ Laser," Fifth International Conference of Laser Medicine and Surgery, Detroit 1983, in an abstract. Thus the nonspecificity of prior art laser treatment of port wine stains is both documented and explainable by the relatively long irradiation times causing massive long-distance thermal diffusion for argon lasers and the nonspecific absorption for CO₂ lasers.

By contrast ultrashort laser pulses have been used. Studies by R. R. Anderson and J. A. Parish entitled "Microvasculature Can Be Selectively Damaged Using Dye Lasers: A Basic Theory in Experimental Evidence in Human Skin," *Lasers in Surgery and Medicine,* 1981, Volume 1, pps. 263–276, show that when utilizing pulse dye lasers with fluence level on the order of 3 to 5 Joules/cm² and exposure times of approximately 300 nanoseconds (ns) target specific damage may be produced in normal blood vessels. The wavelength used was 577 nanometers. While the above pulse width was short enough to restrict thermal diffusion to a small portion of the individual erythrocytes having typical dimensions of 7–15 micrometers carrying the hemoglobin, and thermal diffusion subsequent to the pulse could have allowed heating of the containing vessel without damage to the surrounding tissues, the short 300-nanosecond duration caused the vessels to burst and to spew forth blood. It is possible that a shock wave produced by the ultrashort pulse ruptured the blood vessels causing formation of purpura. Since the vessels are 50μ in diameter and the wall is about 1μ thick, the pulse is so short that only the hemoglobin itself (which is the optical absorber) and any spot on the inner edge of the wall which happens to be in intimate thermal contact with the hemoglobin bearing portion of an erythrocyte are heated during the pulse. After the pulse, the peak temperature achieved within the vessel decays as heat diffuses away. While regions outside the vessel are in fact heated as this diffusion occurs, it is not possible to achieve thermal damage to an adequate depth to insure permanent vessel necrosis.

Note that at the present time several microseconds is the longest pulse time available from commercial pulsed dye lasers. This is still too short to achieve the desired effect.

In summary, it will be appreciated that the difficulty in the prior art methods of utilizing argon laser treatment lies not in the wavelength, at least for low melanin skins, but in the exposure time utilized. The argon lasers are CW lasers which are mechanically shuttered to provide pulsewidths which may vary from 20 milliseconds to 100 milliseconds or more. Even the shortest of these exposure times, 20 milliseconds, results in thermal diffusion to a length of 100 micrometers which is equal to the average spacing between targets. Thus, even if the laser power is initially absorbed only in the target volumes, thermal diffusion during the laser pulse itself provides nearly uniform heating of the entire irradiated area. In order to achieve true specificity, damaging only the target vessels, the exposure time must be limited to about one millisecond or less, which is too short to be achieved with the mechanical shutters presently in use. Additionally, nanosecond pulses from dye lasers cause blood vessel rupture and causes only partial necrosis. Thus these techniques are not optimally useful in treating port wine stains.

Note the following U.S. patents deal with scanning lasers: U.S. Pat. Nos. 3,362,007; 3,642,007; 4,069,823; and 4,316,467; whereas U.S. patents dealing with coaxial bilaser beams include U.S. Pat. Nos. 3,456,651; 3,710,798; 3,769,963; 3,906,953; 3,910,276; 4,240,431 and 4,408,602. Finally, U.S. Pat. No. 3,434,476 deals with a plasma arc scalpel.

SUMMARY OF THE INVENTION

In order to limit thermal diffusion, apparatus is provided which moves the focused laser beam in a circle or other path which controls dosimetry of radiation applied to a target area, with the scanning rate being adjusted to limit thermal diffusion from the irradiated target site for selective target specific energy deposition. In one embodiment, a hand piece is used in which the scanning is provided by rotating optics within the hand piece, with the speed of rotation determining the scanning rate. In an alternative embodiment the scanning may be provided by a rigidly mounted head containing the scanning optics. When used for dermatologic purposes, the adjustable scanning mechanism prevents radiation from impinging on tissue for more than about one millisecond in one embodiment for the selective necrosis of highly-filled port wine stain blood vessels, while leaving adjacent tissue undamaged. The dwell time of the laser beam is designed to match the thermal diffusion time for destruction of the wall of the abnormal vessels, and some surrounding collagen with the dwell time adjusted by the scanning rate. Neither the small, empty normal vessels nor the collagen adjacent the normal vessels are attacked by the impinging radiation since they contain no absorbing chromophore. In one embodiment, a CW laser is used, with time per scan being maintained at less than 60 milliseconds to give the visual impression of a continuous ring of light to the operator, with a rotary scan diameter of 2.8 millimeters and a focal spot size of 0.14 millimeters. The wavelength of the laser is held below 600 micrometers so that the hemoglobin in the erythrocytes absorb sufficient radiation for the necrosis of the vessels containing the erythrocytes. While the subject invention will be described in connection with CW lasers, pulsed lasers may be used and are within the scope of this invention.

In one embodiment the simple hand piece for a CW laser is provided with cooling apparatus involving a cooling ejectant line and a cooling suction line on opposite sides of the nose of the hand-held device. In a further embodiment, bleachable indicators are painted onto the skin prior to usage to indicate to the operator what areas of the epidermis have been irradiated.

It has also been found that to reduce the chances for regeneration of a lesion it is possible to slightly lengthen the pulse which is delivered to the given target area extending the thermal damage into the collagen immediately surrounding the abnormal vessel. An exposure time of about one millisecond allows heating as far as 20 micrometers from the edge of the abnormal vessel. This is adequate to insure total vessel destruction but is still small compared with the spacing between vessels, insuring sparing of a significant volume of the dermis. The exact exposure time involves the correlation between the length of thermal diffusion damage and redevelopment or final destruction of the lesion. Other considerations include the fluence level of the focused light required to produce the desired damage effect and the depth of field, it being understood that the target tissue must be raised to an adequate temperature for a sufficient length of time to produce thermal necrosis.

In order to achieve adequate fluence levels from available laser systems, the laser beam diameter and depth of field are controlled by any of a variety of focusing techniques. The depth of field is made large enough to compensate for any variation in the distance between the target and the delivery system whether this distance is maintained by a mechanical fixture or simply by the operator's hand. Note that a larger depth of field makes the control of the distance between the delivery system and the skin less difficult. The larger depth of field is also useful because, when the skin is depressed by as little as one millimeter by the nose of the tool, this can cause a 1 millimeter bulge inside the nose of the instrument.

Other uses for the subject invention include the treatment of other cutaneous vascular lesions such as telangiectasias, nevus araneus, strawberry nevus, cavernous hemangiomas, cherry hemangiomas, and venous lakes. The treatment of deep, cavernous hemangiomas is expected to require multiple treatments since these lesions are so hypertrophic that vessels nearest to the surface will optically shield underlying vessels. By causing thermal necrosis of the surface vessels and permitting adequate time for phagocytic removal of the necrotic tissue, the next layer of vessels is made vulnerable to the laser irradiation. It should be noted that laser wavelength may also be a more important consideration in treating very deep lesions since very strongly absorbed wavelengths will provide shallower depth of necrosis per treatment. Another use for the invention is in the treatment of psoriasis. Psoriasis is characterized by an abnormal, ectatic and hypertrophic vasculature, along with other abnormal features. Selective destruction of the vascular component permits destruction of the lesion without subsequent tissue inflammation and psoriatic regeneration.

The device is also useful in the treatment of various forms of neovascularization of the eye including diabetic retinopathy and senile macular degeneracy. For this type of lesion a microscopic rather than hand held delivery system is required. In the case of retinal disorders, where melanin absorption in the retinal pigment epithelium could cause undesirable remote heating, a line scan, operator defined and computer controlled, allowing the scan to exactly follow the vascular line would be preferable. However, even full area scanning would destroy less tissue than present modalities for treating each of these diseases. The currently accepted modality calls for intentional destruction of large tissue volumes to reduce the production of angiogenic substances. The scanner described herein, however, has the potential to limit damage to such small volumes that frequently repeated treatments, with greater preservation of visual acuity may be possible.

Another use for the device is in the treatment of structures bearing melanosomes, including actinic keratoses, lentigo, malignant melanomas, and freckles. In this case the dwell time (i.e., scanning rate) is adjusted to destroy the melanosome bearing cells, leaving adjacent cells unharmed.

BRIEF DESCRIPTION OF THE DRAWINGS

These and other features of the subject invention will be better understood in connection with the detailed description taken in conjunction of which.

DETAILED DESCRIPTION

Figure 1:
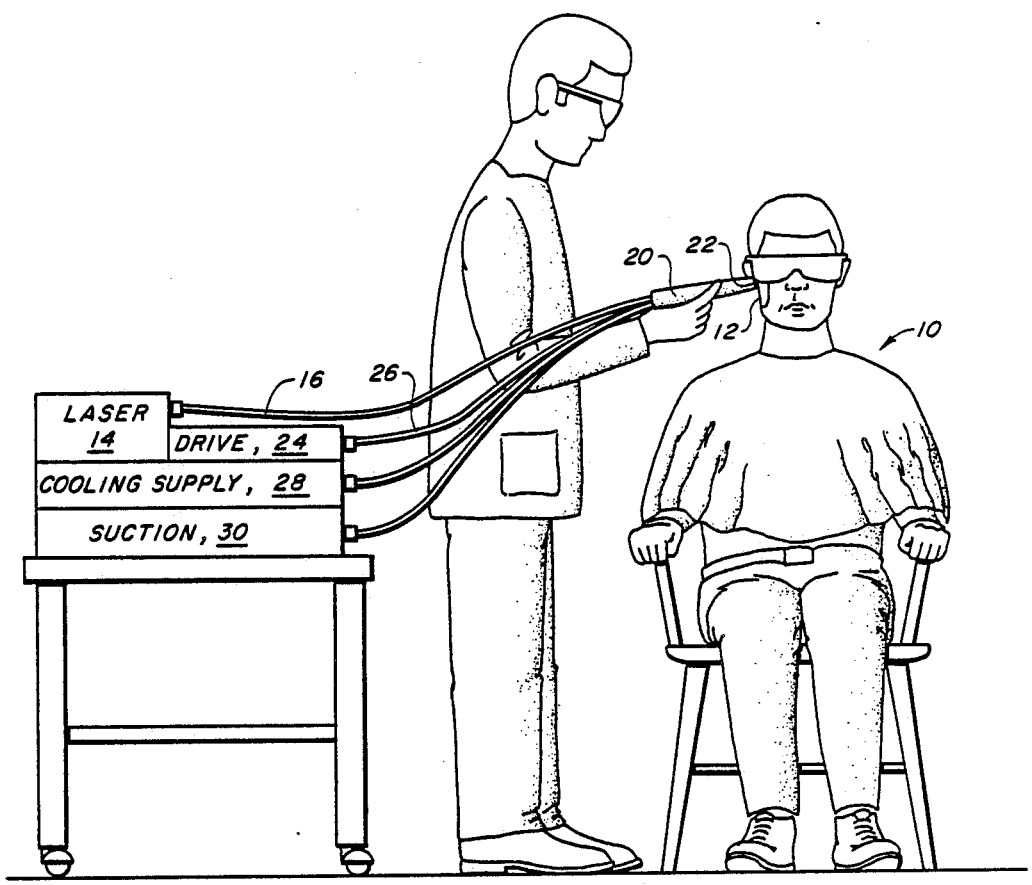
FIG. 1 is diagrammatic representation of the utilization of the scanning hand piece in the treatment of a typical port wine stain.

Referring now to FIG. 1, in one embodiment of a patient 10 having a port wine stain 12 is being treated by laser radiation from a laser source 14 which is channeled by fiber optic cable 16 to a hand-held unit 20 which has therein internal optics utilized to provide scanning of a beam within the nose portion 22 of the tool. This is accomplished in one embodiment through drive motor 24 utilized to control the scan speed by rotating cable 26 which drives a hollow cylindrical barrel in the tool that carries the focusing optics. Alternatively, air drive motors or small electrical motors may be used in the hand piece to drive the rotating optics. Hollow shaft motors (either electrically or pneumatically driven) may incorporate the optical path within the hollow shaft, supporting the rotating element on the end of the shaft. Solid shaft motors must be used with gear or other coupling mechanisms to drive the rotating element. An optional source of cooling liquid 28 is applied to the hand tool which is channeled to the nose portion 22 and is removed by a suction unit 30 such that the area of the target adjacent the nose of the tool is cooled.

Figure 2:
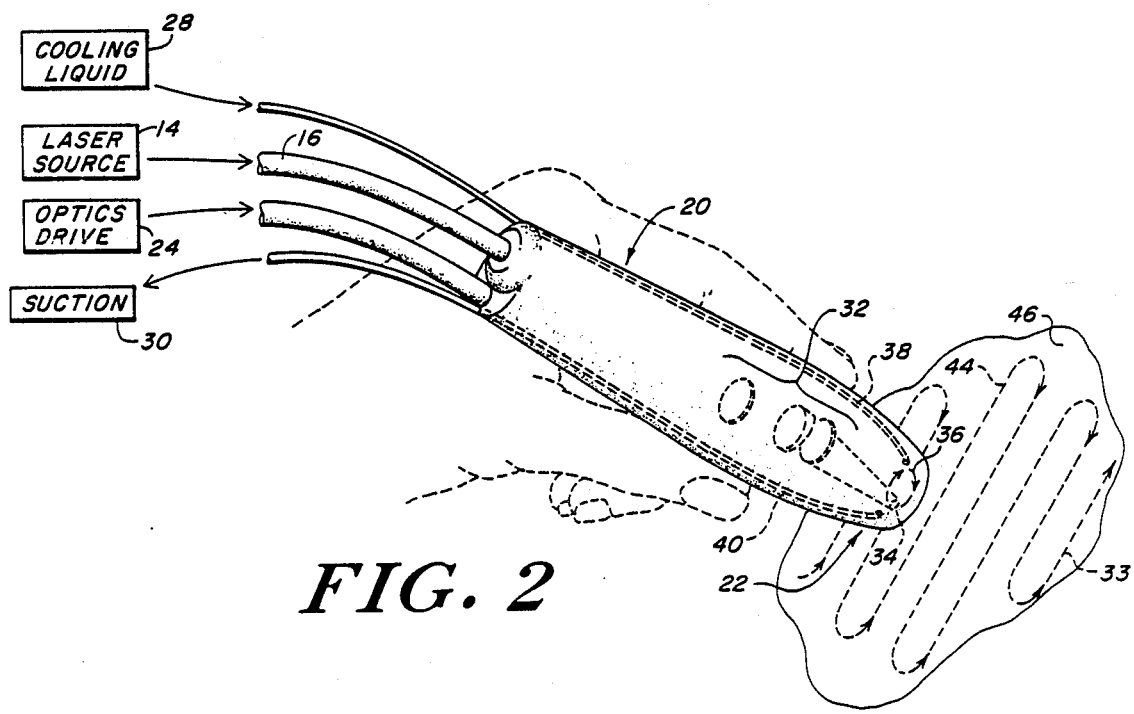
FIG. 2 is a diagrammatic illustration of the operation of the hand piece of FIG. 1 illustrating a focal spot which moves around in a circular scan within the nose of the hand piece while the hand piece is moved across the area to be irradiated, liquid cooling and suction pipes being utilized to provide fluid which cools the irradiated area.

The operation of the hand tool can be better seen in conjunction with FIG. 2 in which like reference characters are utilized between FIGS. 1 and 2. In FIG. 2 an optical system 32 is utilized to focus and rotate a focal spot 34 such that in the illustrated embodiment the spot rotates in a circle 36 as illustrated by the dotted arrow. Cooling fluid is delivered at one side of nose 22 by a delivery tube 38 and is removed by a suction tube 40 as illustrated.

It is the purpose of the rotating optics within the hand tool to scan the focal spot such that it resides over a target for no longer than about one millisecond in one embodiment. The control of the scan rate controls the time with the focused spot resides at a given location within the target area and is readily adjustable by the scan rate. While a circular scan is illustrated in the embodiment of FIG. 2, it will be appreciated that raster scan, Rosette type, orbital, elliptical, or other scan patterns scans may be performed by optics to prevent the focal spot from residing at any given location for longer than a predetermined period of time. In one embodiment the depth of field is made greater than two millimeters by virtue of the focal system aperture utilized. In this embodiment, a focal spot size of 0.14 millimeters, a scan pattern diameter of 2.8 millimeters, and a scan rate of less than 60 milliseconds per cycle are used. For port wine stains, the wavelength of the laser is held below 600 micrometers so that the hemoglobin in the erythrocytes absorbs sufficient radiation to provide for the necrosis of the vessels containing the chromophores.

In one operative mode, the hand piece is moved in a serpentine fashion as illustrated by dotted arrow 33 across an area 46 which corresponds to the area of the port wine stain.

As mentioned before, a dye may be first applied to the affected area which changes color upon irradiation by focal spot 34 such that the treated area may be ascertained with a high degree of certainty. This aids the operator who may be unable to "see" which areas have been treated since the treatment is so gentle as to provide minimal visible color change of the lesion. The actual lightening of the lesion occurs slowly, over a period of days to weeks as the body phagocytizes the necrotic tissue. Instead of a hand held unit, the same treatment may be provided by a programmed scanner. In such a case the indicating dye would not be necessary.

Figure 3A:
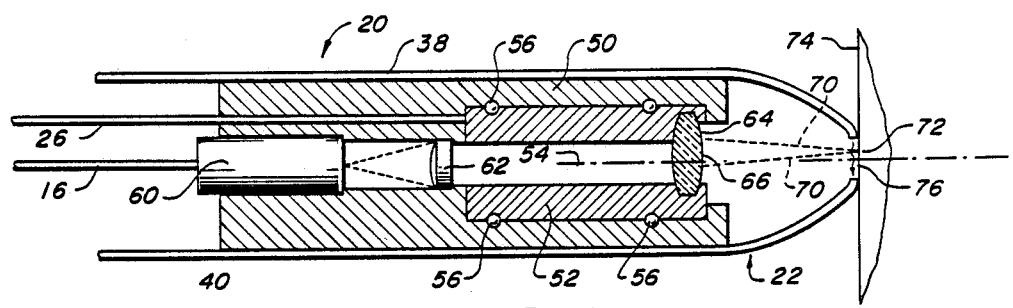
FIG. 3A is a cross-sectional and diagrammatic illustration of one embodiment of the hand piece in which a rotting offset lens is utilized to scan the focused beam in a circular pattern.

Referring to FIG. 3A, hand tool 20 may take on a configuration in which a body or housing 50 includes a hollow cylindrical barrel illustrated at 52 to be rotated via cable 26 or other means about an axis 54 which is typically the central axis of the hand tool. The barrel is supported via a bearing system generally indicated by bearings 56.

Laser radiation is transmitted to the hand tool via fiber optic cable 16 which is coupled via a cable termination 60 to a lens 62 which collimates the light generally along axis 54. A lens 64 having a convex surface 66 focuses the parallel light as indicated by dotted lines 70 to a point 72 on the surface of skin 74. Since the optical axis of the lens is offset from centerline 54, its rotation via a barrel 52 causes the focal spot 72 to rotate on the surface of the skin 74. As can be seen, cooling liquid may be introduced through tube 38 such that liquid proceeds across the irradiated areas illustrated by 76 to suction tube 40.

Figure 3B:
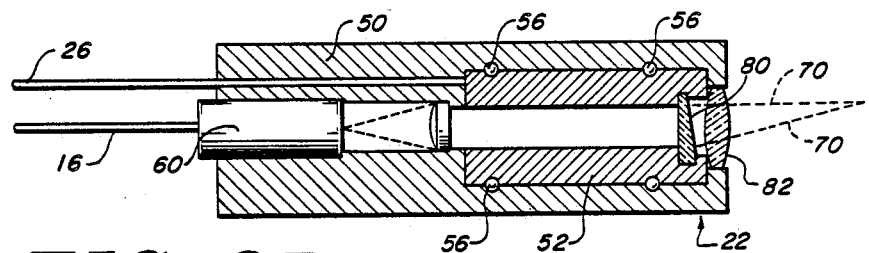
FIG. 3B is a diagrammatic and cross-sectional illustration of an alternative device utilized for the scanning of the beam by providing a rotating optical wedge interposed in the optical path.
Figure 4:
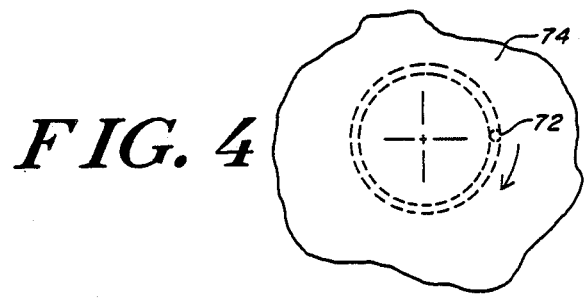
FIG. 4 is a top view and schematic diagram of the circular scan produced by the hand pieces of FIG. 3A and FIG. 3B.

The same system may include as a scanning means an optical wedge 80 which is shown in FIG. 3B in which like apparatus is given like reference characters vis-a-vis FIG. 3A. Note that power to rotate each of the barrels of FIGS. 3A and 3B is delivered by line 26, be it mechanical, electrical, hydraulic, or pneumatic. Note also that a fixed lens 82 is provided in nose 22 of the hand tool to achieve focusing.

Indeed, any focusing optics which is moved so as to provide a scanning beam, be it a raster scan, a circular scan, a line scan, or an elliptical scan, or some combination of these is within the scope of this invention. It is only important that the focal spot 72 not remain over any point within a target area 74 for any longer than is necessary for the particular purpose intended. For port wine stains this means that the dwell time for the spot should be on the order of one millisecond in order to prevent the type of damage which will now be described.

Prior to describing the damage done by thermal diffusion for radiation impinging upon the skin for too long a period of time and referring now to FIG. 5, when using ultrashort pulses to treat port wine stains, it will be appreciated that the abnormal, ectatic vessels are those illustrated by reference character 92. Each of these vessels is nearly completely filled with blood and has a wall 94 thickness of approximately 1-2 microns. Normal blood cells are indicated by reference character 96 and are shown to be approximately 1/10 the size of the inflated port wine vessels, with the spacing between the vessels being approximately 100 microns and with the diameter of the port wine stain vessels being 50 microns, whereas the average diameter of the normal vessels is approximately 5 microns. This is, of course a highly schematic illustration, using "average" values. Actual vessel sizes and spacings vary widely.

What happens with the ultra-short pulses is that the thermal diffusion as illustrated by arrows 102 is not sufficiently long to necrose both the blood in the port wine stain vessel as well as the vessel wall. Rather what happens is that the vessel wall is ruptured due to the ultrashort pulse thereby bursting the vessel and causing blood to spurt out as illustrated at 104. This is highly undesirable due primarily to the fact that the blood spurting through the surrounding tissue here illustrated by reference character 100, interferes with further irradiation. In addition this point pulsed irradiation is very tedious for the operator.

Figure 6:
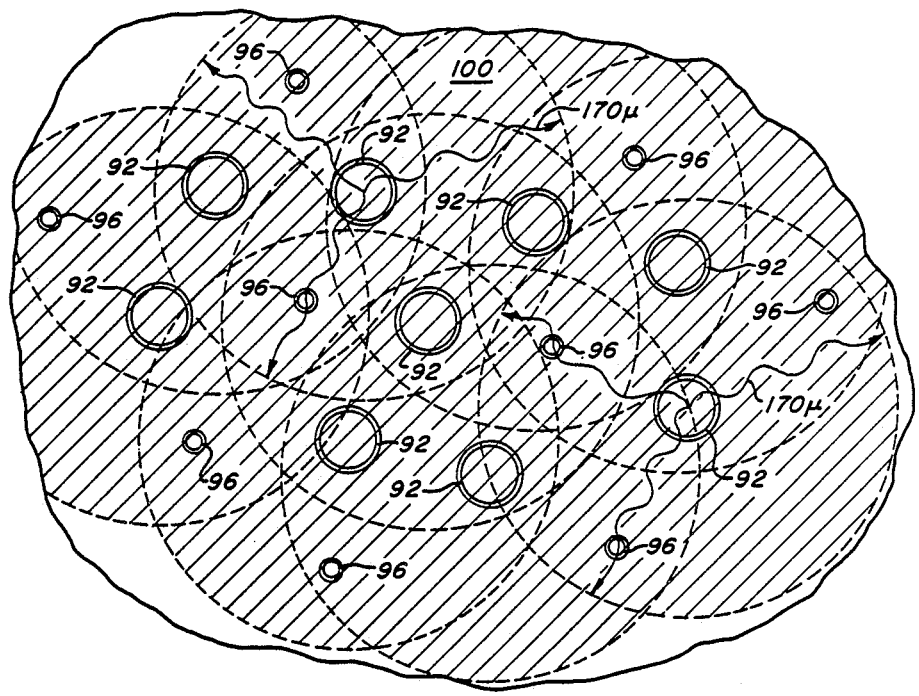
FIG. 6 is a diagrammatic representation of the result of irradiation of a port wine stain with a prior art CW or long pulse laser showing complete necrosis of all irradiated areas.

Referring to FIG. 6, CW or a long pulse radiation causes a necrosis not only of the blood within the port wine stain vessels 92 but also necroses the collagen between the vessels as well as normal vessels 96. For example, a 50 msec pulse gives 170 micron thermal diffusion length from each absorbing vessel, such that there is an overlap in the manner illustrated, with the result that the entire irradiated area is damaged as shown by the shading.

Figure 7:
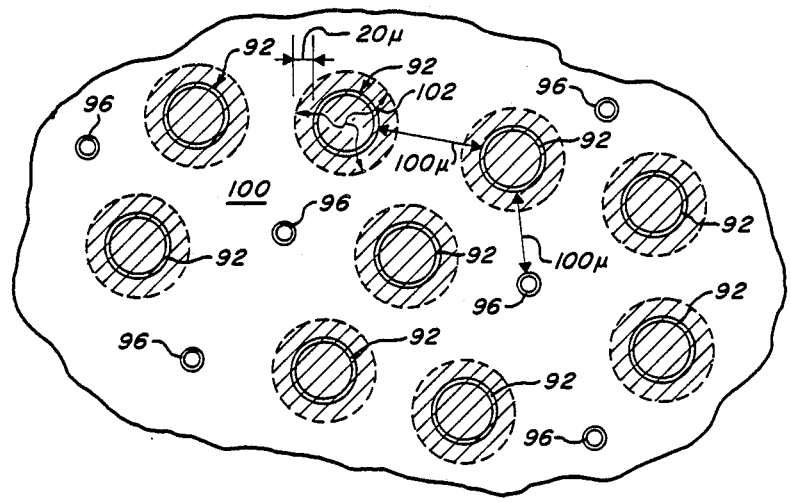
FIG. 7 is a diagrammatic representation of the result of utilizing the subject scanning system in which thermal diffusion is limited, causing necrosis of the port wine stain blood vessel, its wall and a very small portion of the collagen immediately adjacent the vessel wall, without disruption of the majority of the normal tissue within the port wine stain area.

Referring now to FIG. 7, when the dwell time for the radiation is limited to approximately one millisecond in the subject system, the area necrosed is indicated to include the port wine stain vessel 92 and extends approximately 20 micrometers (microns) into the tissue immediately adjacent the port wine stain vessels. It will be noted that little of surrounding tissue 100 and few of the normal vessels 96 are affected. The subject technique thus leads to a relatively painless, treatment for the port wine stain syndrome, without extensive tissue damage, sloughing, and scab formation.

Damage induced by thermal diffusion as illustrated by wavy arrows 102 may be controlled in length by viture of the spot size and the scanning time, which is controllable to the extent necessary to preclude damage to the majority of the avascular tissue and the normal blood vessels within the port wine stain. As mentioned before, for a focal spot size of 0.14 millimeters and a scan diameter of 2.8 millimeters with a cycle time 60 milliseconds, even without the utilization of external cooling, the necrosed area is limited to 20 microns from the walls of the vessels which are enlarged and are filled with blood, whereas the vessels that are normal and generally less than 10 percent of which are filled with blood at any point in time, are virtually uneffected. Note that the aforempotional cooling may be added for patient comfort, to avoid the use of anesthetic, and to increase the specificity of the treatment.

Figure 5:
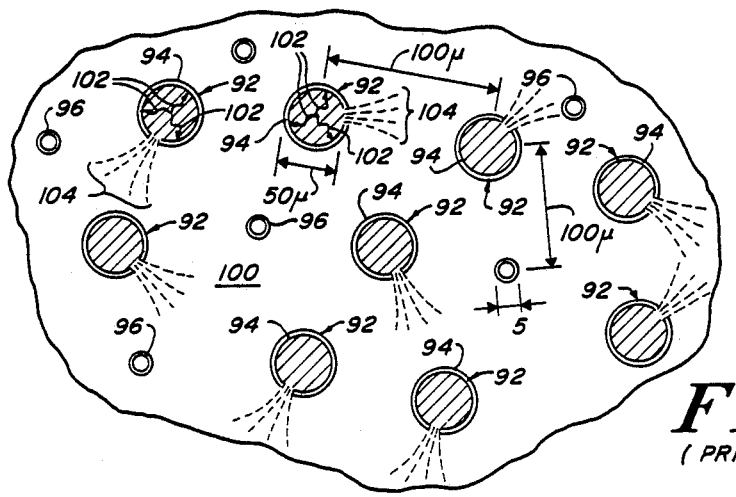
FIG. 5 is a diagrammatic representation of the result of irradiation of a port wine stain with the prior art ultrashort laser pulses, illustrating the rupturing of the port wine stain blood vessels causing the spewing forth of blood.

It will be appreciated that one difference between the subject treatment and that of FIG. 5 is that the abnormal vessel is necrosed without the spurting forth of blood which decreases the effectiveness of treatment. The present technique is more effective than completely necrosing the whole port wine stain area because the sloughing associated with the prior art technique of FIG. 6 is eliminated. Thus a painful and time-consuming procedure is replaced through the utilization of the control of the dwell time of the radiation impinging on the target area to an extent not heretofore possible, thereby effectuating a treatment that may be used without anesthetic and which achieves the desired result without large amounts of scabbing and sloughing.

It will be appreciated that the control of laser radiation through the scanning device described in this invention is applicable to other situations which require a controlled amount of energy be delivered to a given absorbing target site. Thus for instance the subject technique is applicable to treatment of any abnormal, ectatic vasculature, any highly filled vasculature within tissue, any preferentially stained (for laser absorption) target tissue whether or not embedded in normal tissue to be spared. With appropriate choice of laser wavelength it may be used to destroy non-vascular pigmented targets, in particular melanin bearing tissues such as actinic keratosis, lentigo, malignant melanoma, or portions of the retinal pigment epithelium.

Having above indicated a preferred embodiment of the present invention, it will occur to those skilled in the art that modifications and alternatives can be practiced within the spirit of the invention. It is accordingly intended to define the scope of the invention only as indicated in the following claims:

What is claimed is:

1. A system for use in living tissue or cells in the medical treatment of certain conditions by the selective necrosis of a target material including blood vessels, melanin bearing, or other naturally or artificially pigmented tissues or cells, said system comprising:
    means including a laser for generating a beam of laser radiation;
    a housing;
    laser beam applying means within said housing, in communication with said laser beam generating means, for controlling the dosimetry of laser radiation applied to the target material, said applying means including:
    means within said housing for directing the beam of laser radiation along an optical path within said applying means;
    means within said housing, positioned along the optical path, for focusing the beam of laser radiation onto the target material as a focused spot of laser radiation having a desired shape, dimension and intensity;
    scanning means, within said housing and coupled to said directing means and to said focusing means, for automatically causing the laser beam to deviate from its optical path in such a way that the focused spot of laser radiation is moved at a rate in a desired pattern within an area containing the target material; and
    means for controlling the rate at which the scanning means moves the focused laser radiation spot, and the intensity of the radiation in the focused laser spot, thereby controlling the laser energy absorbed by the target material by regulating a dwell time of the focused laser spot to produce a thermal diffusion into the target material, which causes necrosis of the target material while tissues and cells other than the target material are substantially unaffected.

2. The system of claim 1, wherein the dwell time is adjusted to match the thermal diffusion time for heat within the target material.

3. The system of claim 1, wherein the dwell time is sufficient to provide thermal diffusion into collagen positioned adjacent to the target material.

4. The system of claim 1, wherein the dwell time is sufficient relative to the intensity of the laser radiation to raise the temperature of the target material for a sufficient length of time to produce thermal necrosis thereof.

5. The system of claim 4, wherein said focussing means includes means for defining laser radiation intensity as a function of spot diameter and a depth of field of the laser radiation as focused to the spot.

6. The system of claim 1, wherein the controlling means regulates the scanning means to move the spot of laser radiation at a rate to achieve the desired dwell time.

7. The system of claim 1 wherein said housing is configured and sized for hand operation.

8. The system of claim 1 wherein said laser beam applying means is provided with cooling means.

9. The system of claim 1 wherein said scanning means causes the focused spot of laser radiation to move in a circular pattern on the target material.

10. The system of claim 9 wherein said scanning means comprises a hollow rotatable shaft having an access; said system further comprises means for rotating said shaft; and said focusing means is mounted in said hollow shaft at a non-perpendicular angle to said access, so as to provide a rotary scan of the focused spot on the target material as said shaft is rotated.

11. The system of claim 10 wherein said focusing means is a lens.

12. The system of claim 9 wherein said scanning means comprises a hollow rotatable shaft having an access, and an optical wedge mounted in said hollow shaft; said system further comprising means for rotating said shaft; and said focusing means including a fixed lens located after the optical wedge in the optical path.

* * * * *

UNITED STATES PATENT AND TRADEMARK OFFICE
CERTIFICATE OF CORRECTION

PATENT NO. : 4,733,660
DATED : March 29, 1988
INVENTOR(S) : Irving Itzkan

It is certified that error appears in the above-identified patent and that said Letters Patent is hereby corrected as shown below:

Column 3, line 12, "that" should read --than--.

Column 4, line 53, "with time" should read --with the time--.

Column 6, line 30, "rotting" should read --rotating--.

Column 6, line 57, "embodiment of a" should read --embodiment a--.

Column 7, line 24, "time with" should read --time that--.

Column 8, line 55, "this point pulsed" should read --this point by point pulsed--.

Column 9, line 21, "uneffected." should read --unaffected.--.

Signed and Sealed this

Thirtieth Day of May, 1989

Attest:

DONALD J. QUIGG

Attesting Officer

Commissioner of Patents and Trademarks